(12) United States Patent
Pauly et al.

(10) Patent No.: US 7,105,184 B2
(45) Date of Patent: Sep. 12, 2006

(54) **COSMETIC AND/OR DERMOPHARMACEUTICAL PREPARATIONS CONTAINING LEAF EXTRACTS OF THE PLANT *ARGANIA SPINOSA***

(75) Inventors: Gilles Pauly, Nancy (FR); Florence Henry, Villers-les-Nancy (FR); Louis Danoux, Saulxures les Nancy (FR); Zoubida Charrouf, Rabat R.P. (MA)

(73) Assignee: Cognis France S.A., Saint-Martory (FR)

( * ) Notice: Subject to any disclaimer, the term of this patent is extended or adjusted under 35 U.S.C. 154(b) by 151 days.

(21) Appl. No.: 10/450,008

(22) PCT Filed: Nov. 28, 2001

(86) PCT No.: PCT/EP01/13885

§ 371 (c)(1),
(2), (4) Date: Jun. 6, 2003

(87) PCT Pub. No.: WO02/45728

PCT Pub. Date: Jun. 13, 2002

(65) Prior Publication Data

US 2004/0047832 A1    Mar. 11, 2004

(30) Foreign Application Priority Data

Dec. 6, 2000 (EP) .................. 00440319

(51) Int. Cl.
*A01N 65/00* (2006.01)
(52) U.S. Cl. .................................................. 424/725
(58) Field of Classification Search ............... 424/725
See application file for complete search history.

(56) References Cited

U.S. PATENT DOCUMENTS

| | | | |
|---|---|---|---|
| 4,172,887 A | 10/1979 | Vanlerberghe et al. | |
| 5,211,944 A | 5/1993 | Tempesta | |
| 5,612,021 A * | 3/1997 | Mellul | 424/61 |
| 5,650,137 A * | 7/1997 | Nguyen et al. | 424/59 |
| 5,705,169 A | 1/1998 | Stein et al. | |
| 5,730,960 A | 3/1998 | Stein et al. | |
| 5,925,363 A * | 7/1999 | Colin et al. | 424/401 |
| 5,945,091 A | 8/1999 | Habeck et al. | |
| 6,110,447 A * | 8/2000 | Ramin et al. | 424/61 |
| 6,187,323 B1 * | 2/2001 | Aiache et al. | 424/401 |
| 6,193,960 B1 | 2/2001 | Metzger et al. | |
| 6,280,756 B1 * | 8/2001 | Ramin et al. | 424/401 |
| 2003/0138394 A1 | 7/2003 | Charrouf et al. | |

FOREIGN PATENT DOCUMENTS

| | | |
|---|---|---|
| DE | 1 165 574 | 8/1960 |
| DE | 20 24 051 | 5/1970 |
| DE | 197 56 377 | 12/1997 |
| DE | 197 12 033 | 9/1998 |
| EP | 0 496 649 | 7/1992 |
| EP | 0 545 147 | 6/1993 |
| EP | 0 694 521 | 1/1996 |
| EP | 0 818 450 | 1/1998 |
| EP | 0 693 471 | 11/2000 |
| FR | 2 252 840 | 11/1974 |
| FR | 2500306 * | 8/1982 |
| FR | 2553788 * | 4/1985 |
| FR | 2724663 * | 3/1996 |
| FR | 002756183 * | 5/1998 |
| GB | 962919 | 7/1964 |
| GB | 1333475 | 10/1973 |
| JP | 02-204417 A | 8/1990 |
| JP | 02-204495 A | 8/1990 |
| JP | 03-005423 A | 1/1991 |
| JP | 03-093782 A | 4/1991 |
| JP | 03-255015 A | 11/1991 |
| JP | 04-029934 A | 1/1992 |
| JP | 05 255060 | 10/1993 |
| JP | 10 218780 | 8/1998 |
| NZ | 264 108 | 5/1997 |
| WO | 0 768 079 | 4/1997 |
| WO | WO 98 19651 | 5/1998 |
| WO | WO 00 69404 | 11/2000 |
| WO | WO 01/82885 A1 | 11/2001 |

OTHER PUBLICATIONS

Tahrouch et al., Acta Botanica Gallica, 1998, 145(4), 259-63, abstract only.*
Tahrouch et al., Acta Botanica Gallica, 2000, 147(3), 225-232, abstract only.*
Tahrouch et al., "Polyphenol investigation of *Argania spinosa* (Sapotaceae) endemic tree from Morocco", Acta Botanica Gallica, vol. 147, 2000, pp. 225-232, abstract, p. 228 XP000996078.
J.Falbe, "Surfactants in Consumer Products", Springer Verlag, Berlin, (1987), pp. 54-124.
R. Lochhead et al., "Encyclopedia of Polymers and Thickeners for Cosmetics", Cosmetics & Toiletries, vol. 108, (May 1993), pp. 95-135.
C. Todd et al., "Volatile silicone fluids for cosmetic formulations", Cosmetics and Toiletries, vol. 91 (Jan. 1976), pp. 29-32.
Maurin, "L'huile d'Argan Argania spinosa (L.) Skeels Sapotaceae" Revue Francaise des Corps Gras, vol. 39, No. 5-6, (May-Jun., 1992), pp. 139-146, abstract only.
Alaoul et al., "Activite analgesique et anti-inflammatoire des saponines d'Argania spinosa", Ann. Pharmaceeutiques Francaises, vol. 56, No. 5, (1998), pp. 220-228, abstract only.

* cited by examiner

*Primary Examiner*—Michael Meller
(74) *Attorney, Agent, or Firm*—John F. Daniels; Daniel S. Ortiz

(57) ABSTRACT

A cosmetic and/or dermopharmaceutical composition containing an extract selected from the group consisting of flavone derivatives, saponosides, oligomeric procyanolidones, sterols, and mixtures thereof, all of which are derived from an *Argania spinosa* plant.

4 Claims, No Drawings

COSMETIC AND/OR DERMOPHARMACEUTICAL PREPARATIONS CONTAINING LEAF EXTRACTS OF THE PLANT *ARGANIA SPINOSA*

BACKGROUND OF THE INVENTION

This application is a 371 of PCT/EP01/13885 filed Nov. 28, 2001.

The invention is in the field of care substances and relates to compositions comprising leaf extracts of the plant *Argania spinosa*, and to the use of leaf extracts of the plant *Argania spinosa* as novel skincare and haircare agents.

Cosmetic preparations are available to the consumer nowadays in a large number of combinations. In this connection, it is not only expected that these cosmetics demonstrate a certain care effect or overcome a certain deficiency, but demand is more and more often for products which have several properties simultaneously and thus exhibit an improved performance spectrum. Of particular interest are substances which both represent active ingredients which impart, for example, care, revitalizing properties which protect against aging phenomena for skin and/or hair, and also simultaneously have a positive influence on or at least do not impair the technical properties of the cosmetic product, such as storage stability, photostability and ability to be formulated. In this connection, good skin compatibility and particularly the use of natural products is additionally requested by customers. In addition, it is desirable, by combining already known active ingredients, or by discovering new fields of use for classes of substance which are already known, to obtain significantly better products. However, a disadvantage often exists here that a combination of active ingredients is only obtained if different plant extracts are used simultaneously in varying quantitative ratios.

Extracts from plants and their ingredients are being used more and more often in cosmetics and pharmacy. Plant extracts have been used for many years in a very wide variety of cultures for medicinal and also even for cosmetic purposes. Often, only very specific individual effects for these plant extracts were known, and the field of use was very limited.

DESCRIPTION OF THE INVENTION

The object of the present patent application was to provide cosmetic and/or dermopharmaceutical preparations which permit a use in cosmetics or else in pharmacy and, as well as care properties, primarily have improved protecting properties for human skin and/or hair, for example against UV radiation and other environmental influences and at the same time exhibit a preventative and healing effect in cases of aging phenomena of the skin, which can influence melanogenesis and can be used in an antiinflammatory capacity.

A further object of the present patent application was to provide preparations which comprise active ingredients from renewable raw materials and at the same time can be used widely as care agents in cosmetics both in skin cosmetics and also in haircare.

The invention provides preparations which comprise leaf extracts of the plant *Argania spinosa* as care agents for skin and hair.

Surprisingly, it has been found that by using leaf extracts of the plant *Argania spinosa*, products are obtained which simultaneously have good care and protecting properties for skin and hair, and also have high skin compatibility. The agents obtained in this way are characterized by particularly good effects in skin cosmetics. As well as protecting effects, they also exhibit a preventative and healing effect in cases of aging phenomena of the skin. They influence melano-genesis and exhibit an antiinflammatory and anti-microbial activity.

These multiple fields of use of the agents according to the invention from the renewable raw material of the plant *Argania spinosa* makes it very attractive for the market and for the consumer. The complex object of the invention could therefore be achieved through the use of leaf extracts of the plant *Argania spinosa*.

For the purposes of the invention, the term "preparations" is used synonymously with the term "agents" or "care agents".

*Argania spinosa*

The extracts to be used according to the invention are obtained from the leaves of a plant of the Sapotaceae family, specifically from *Argania spinosa*. This plant is a tree reminiscent of the olive tree which is found predominantly in Morocco on the west side of the Atlas mountain range. On its knurled branches and thorny twigs, it forms berries of the size and shape of olives with one to two seeds. The oil from the seeds, which has a nut-like taste, is used inter alia as a food oil.

Extraction

The extracts to be used according to the invention are prepared by customary methods of extraction of the leaves of the plants. With regard to the suitable conventional extraction methods, such as maceration, remaceration, digestion, agitation maceration, fluidized-bed extraction, ultrasound extraction, countercurrent extraction, percolation, repercolation, evacolation (extraction under reduced pressure), diacolation and solid-liquid extraction under continuous reflux which is carried out in a Soxhlet extractor, each of which is known to the person skilled in the art and any of which can be used in principle, reference may be made by way of example to Hagers Handbuch der Pharmazeutischen Praxis ($5^{th}$ edition, Vol. 2, pp. 1026–1030, Springer Verlag, Berlin-Heidelberg-New York 1991). Starting material which may be used are fresh or dried leaves of the plants, although usually the starting materials are leaves of the plants which can be mechanically comminuted prior to extraction. In this connection, all comminution methods known to the person skilled in the art are suitable, mention being made by way of example to comminution using a device containing blades.

Solvents which can be used for carrying out the extractions are preferably organic solvents, water or mixtures of organic solvents and water, in particular low molecular weight alcohols, esters, ethers, ketones or halogen-containing hydrocarbons with greater or lesser water contents (distilled or undistilled), preferably aqueous, alcoholic solutions with greater or lesser water contents. Particular preference is given to the extraction with water, methanol, ethanol, propanol, butanol and isomers thereof, acetone, propylene glycols, polyethylene glycols, ethyl acetate, dichloromethane, trichloromethane, and mixtures thereof. The extraction usually takes place at 20 to 100° C., preferably at 80 to 100° C., in particular at the boiling temperature of the solvents or solvent mixtures. In one possible embodiment, the extraction is carried out under an inert gas atmosphere to avoid oxidation of the ingredients of the extract. The extraction times are adjusted by the person skilled in the art depending on the starting material, the extraction method, the extraction temperature, the ratio of solvent to raw material, etc. After the extraction, the resulting crude extracts can optionally be subjected to further customary steps, such as, for example, purification, concentration and/or decoloration. If desired, the extracts prepared in this way can, for example, be subjected to selective removal of individual undesired ingredients. The extraction can be carried out to any desired degree of extraction, but is usually carried out exhaustively.

The present invention encompasses the finding that the extraction conditions and also the yields of the end extracts can be chosen depending on the desired field of use.

The amount of plant extracts used in said preparations is governed by the concentration of the individual ingredients and by the type of applications of the extracts. The total amount of the plant extract which is present in the preparations according to the invention is usually 0.01 to 25% by weight, preferably 0.03 to 5% by weight, in particular 0.03 to 0.6% by weight, calculated as dry weight, based on the preparations, with the proviso that the quantitative amounts add up to 100% by weight with water and optionally further auxiliaries and additives.

The total content of auxiliaries and additives may be 1 to 50% by weight, preferably 5 to 40% by weight, based on the cosmetic and/or dermopharmaceutical preparations. The preparations can be prepared by customary cold or hot processes; preference is given to using the phase-inversion temperature method.

For the purposes of the invention, active substance refers to the proportion of substances and also auxiliaries and additives which are present in the composition, with the exception of the additionally added water.

Extracts

The leaf extracts of the plant *Argania spinosa* according to the invention generally comprise, as active ingredients, flavone derivatives, saponosides, oligomeric procyanolidines and sterols. They have a composition which varies depending on the starting material chosen and on the extraction method chosen. A particular embodiment of the invention is therefore cosmetic and/or dermopharmaceutical preparations which comprise leaf extracts of *Argania spinosa* which comprise substances chosen from the group formed by flavone derivatives, saponosides, oligomeric procyanolidines and sterols.

For the purposes of the present invention, flavone derivatives are understood as meaning those which can be isolated from the leaves of the plant *Argania spinosa*. In particular, it refers to substances which represent hydrogenation, oxidation or substitution products of 2-phenyl-4H-1-benzopyran, where a hydrogenation in the 2,3-position of the carbon backbone can already be present, an oxidation in the 4-position can already be present, and substitution products are understood as meaning the replacement of one or more hydrogen atoms by hydroxyl or methoxy groups. This definition thus also covers flavans, flavan-3-ols (catechins), flavan-3,4-diols (leucoanthocyanidines), flavones, flavanols and flavanones in the conventional sense. In a particular embodiment of the invention, it refers to glycosidated flavone derivatives, in particular myricetin glycoside, quercetin glycoside, gossypetin glycoside, kaempferol glycoside and luteolin glycoside.

For the purposes of the invention, saponosides are to be understood as meaning those which can be isolated from the leaves of the plant *Argania spinosa*. In particular, it refers to a group of glycosides which form colloidal, soap-like solutions in water.

For the purposes of the invention, sterols are to be understood as meaning steroids which can be isolated from the leaves of the plant *Argania spinosa*. In particular, it refers to spinasterol (Δ7 sterol), scottenol and/or steroids which carry a hydroxyl group only on C-3, but otherwise carry no functional group, i.e. formally represent alcohols. In addition, the sterols containing 27 to 30 carbon atoms generally have a C═C double bond in 5/6 position, more rarely also and/or in 7/8, 8/9 and other positions (e.g. 22/23).

For the purposes of the invention, oligomeric procyanolidines (OPC) are understood as meaning those which can be isolated from the leaves of the plant *Argania spinosa*.

As monomer building blocks, they comprise the tannins widespread in the plant kingdom. In chemical terms, it is possible to differentiate between two types of tannins, namely condensed forms, which include procyanidin A2, and hydrolyzable tannins. Condensed tannins, which are also referred to as flavolans, arise in biosynthesis as a result of condensation of monomers, such as, for example, catechin, gallocatechin, afzelechin (2-R, 3-S type monomers), and epicatechin, epigallocatechin and epiafzelechin (2-R, 3-R type monomers). As a result of condensation of the monomers, firstly dimers and then higher oligomers form, where the condensation takes place through the formation of a C—C bond in 4–8 or 6–8 position. In the case of the preferred A2 dimers of the type proanthocyanidin A2 there is a double bond, namely C2→O→C7 and C4→C8. The structure is shown in the diagram below:

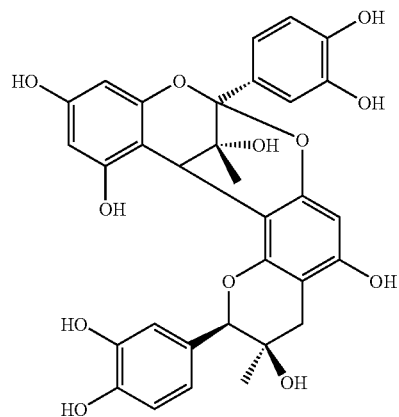

The A2 type proanthocyanidines are less susceptible to hydrolysis than the B types. Moreover, this term is used synonymously for the group of condensed tannins since the latter cleave off monomers under the influence of hot mineral acids.

To increase the stability in formulations, the OPC are preferably derivatized following extraction and the resulting derivatives used in the formulations. Particular preference here is given to the esters with OPC.

The invention further provides for the use of extracts from the leaves of the plant *Argania spinosa* as care agents for the skin and/or the hair. This type of use includes both agents with a cosmetic action and also with a dermopharmaceutical action.

Care Agents:

For the purposes of the invention, care agents are understood as meaning care agents for skin and hair. These care agents include, inter alia, cleansing and restorative action for skin and hair.

Application can be topical or orally in the form of tablets, dragees, capsules, juices, solutions and granules.

The preparations according to the invention moreover exhibit an excellent skincare action coupled with simultaneously high skin compatibility. In addition, they exhibit good stability, in particular toward oxidative decomposition of the products. The preparations have a large number of cosmetic and dermopharmaceutical effects. The invention therefore further provides for the use of extracts from the leaves of the plant *Argania spinosa*

- as sunscreens; in particular against UVA radiation and/or against UVB radiation;
- as antioxidant;
- as antiinflammatory agents;
- as antimicrobial agents;
- as agents against skin aging;
- as protease-inhibiting agent, in particular as MMP- and/or collagenase- and/or elastase-inhibiting agent and preferably as plasmin inhibitors;
- as pigmentation agents.

Sunscreens or UV Light Protection Factors

The extracts from the leaves of the plant *Argania spinosa* act as sunscreens for the purposes of the invention.

For the purposes of the invention, sunscreens or UV light protection factors are the terms used for light protection agents which are useful for protecting the human skin against harmful influences of direct and indirect solar radiation. The ultraviolet radiation from the sun which is responsible for tanning the skin is divided into the sections UV-C (wavelengths 200–280 nm), UV-B (280–315 nm) and UV-A (315–400 nm).

The pigmentation of normal skin under the influence of solar radiation, i.e. the formation of melanins, is brought about by UV-B and UV-A in different ways. Irradiation with UV-A rays ("long-wave UV") results in the darkening of the melanin bodies already present in the epidermis, without harmful influences being evident. This is different in the case of so-called "short-wave UV" (UV-B). This brings about the formation of so-called delayed pigment as a result of the new formation of melanin granules. However, before the (protecting) pigment is formed, the skin is subject to the effect of unfiltered radiation which, depending on the exposure time, can lead to the formation of skin redness (erythema), skin inflammations (sunburn) and even blisters.

The UV absorbers or light filters, which thus convert the UV radiation into harmless heat, used are extracts from the leaves of the plant *Argania spinosa*, these can additionally be present in combination with further sunscreens or UV light protection factors.

These further UV light protection factors are, for example, organic substances (light protection filters) which are liquid or crystalline at room temperature and which are able to absorb ultraviolet rays and give off the absorbed energy again in the form of longer-wavelength radiation, e.g. heat. UVB filters can be oil-soluble or water-soluble. Examples of oil-soluble substances are:

3-benzylidenecamphor or 3-benzylidenenorcamphor and derivatives thereof, e.g. 3-(4-methylbenzylidene)-camphor, as described in EP 0693471 B1;

4-aminobenzoic acid derivatives, preferably 2-ethylhexyl 4-(dimethylamino)benzoate, 2-octyl 4-(dimethylamino)benzoate and amyl 4-(dimethylamino)benzoate;

esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylene);

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably di-2-ethylhexyl 4-methoxybenzmalonate;

triazine derivatives, such as, for example, 2,4,6-trianilino (p-carbo-2'-ethyl-1'-hexyloxy)-1,3,5-triazine and octyltriazone, as described in EP 0818450 A1 or dioctylbutamidotriazone (Uvasorb® HEB);

propane-1,3-diones, such as, for example, 1-(4-tertbutylphenyl)-3-(4'-methoxyphenyl)propane-1,3-dione;

ketotricyclo(5.2.1.0)decane derivatives, as described in EP 0694521 B1.

Suitable water-soluble substances are:

2-phenylbenzimidazole-5-sulfonic acid and the alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and its salts;

sulfonic acid derivatives of 3-benzylidenecamphor, such as, for example, 4-(2-oxo-3-bornylidenemethyl)benzenesulfonic acid and 2-methyl-5-(2-oxo-3-bornylidene) sulfonic acid and salts thereof.

Suitable typical UV-A filters are, in particular, derivatives of benzoylmethane, such as, for example, 1-(4'-tert-butylphenyl)-3-(4'-methoxyphenyl)propane-1,3-dione, 4-tert-butyl-4'-methoxydibenzoylmethane (Parsol 1789), 1-phenyl-3-(4'-isopropylphenyl)propane-1,3-dione, and enamine compounds, as described in DE 19712033 A1 (BASF). The UV-A and UV-B filters can of course also be used in mixtures. As well as said soluble substances, insoluble light protection pigments, namely finely dispersed metal oxides or salts, are also suitable for this purpose. Examples of suitable metal oxides are, in particular, zinc oxide and titanium dioxide and also oxides of iron, zirconium, silicon, manganese, aluminum and cerium, and mixtures thereof. Salts which may be used are silicates (talc), barium sulfate or zinc stearate. The oxides and salts are used in the form of the pigments for skincare and skin-protective emulsions. The particles here should have an average diameter of less than 100 nm, preferably between 5 and 50 nm and in particular between 15 and 30 nm. They can have a spherical shape, but it is also possible to use particles which have an ellipsoidal shape or a shape deviating in some other way from the spherical form. The pigments can also be surface-treated, i.e. hydrophilicized or hydrophobicized. Typical examples are coated titanium dioxides, such as, for example, titanium dioxide T 805 (Degussa) or Eusolex® T2000 (Merck). Suitable hydrophobic coating agents are here primarily silicones and, specifically in this case, trialkoxyoctylsilanes or dimethicones. In sunscreens, preference is given to using micro- or nanopigments. Preference is given to using micronized zinc oxide. Further suitable UV light protection filters are given in the review by P. Finkel in SÖFW-Journal 122, 543 (1996) and Parfümerie und Kosmetik. 3 (1999), p. 11 ff.

The extracts from the leaves of the plant *Argania spinosa* are effective, for the purposes of the invention, against the damage to fibroblasts and/or keratinocytes by UVA radiation and/or UVB radiation.

UVA rays penetrate into the dermis, where they lead to oxidative stress, which is demonstrated by a lipoperoxidation of the cytoplasma membranes. The lipoperoxides are degraded to malonaldialdehyde (MDA), which will crosslink many biological molecules such as proteins and nucleic bases (enzyme inhibition or mutagenesis). The extracts of the plant *Argania spinosa* according to the invention significantly reduce the degree of MDA in human fibroblasts which is induced by UVA rays and thus exhibit a high capacity for reducing harmful effects of oxidative stress on the skin.

UVB rays trigger inflammation through activation of an enzyme, namely phospholipase A2 or PLA2. This inflammation (erythema, edema) is triggered by the removal of arachidonic acid from the phospholipids in the plasma membrane by the phospholipase. Arachidonic acid is the precursor of prostaglandins, which cause inflammation and cell membrane damage; the prostaglandins E2 (=PGE2) are formed by cyclooxygenase. The degree of release of the cytoplasm enzyme LDH (lactate dehydrogenase) in human keratinocytes serves as a marker for cell damage.

The extracts from the leaves of the plant *Argania spinosa* according to the invention reduce the effect of UVB radiation on the number of keratinocytes and on the content of released LDH. Accordingly, the extracts have the ability to reduce the damage to cell membranes caused by UVB radiation.

For the purposes of the invention, the extracts from the leaves of the plant *Argania spinosa* act as an antioxidant or free-radical scavenger.

For the purposes of the invention, antioxidants are understood as meaning oxidation inhibitors which can be isolated from the leaves of the plant *Argania spinosa*. Antioxidants are able to inhibit or prevent the undesired changes in the substances to be protected caused by oxygen effects and other oxidative processes. The effect of the antioxidants consists in most cases in them acting as free-radical scavengers for the free radicals which arise during autoxidation.

As well as the use of extracts of the plant *Argania spinosa* as antioxidants, further, already known antioxidants can also be used. A possible use of the antioxidants for example in cosmetic and/or dermopharmaceutical preparations is the use as secondary light protection agents, since antioxidants are able to interrupt the photochemical reaction chain which is triggered when UV radiation penetrates the skin. As well as the plant extract according to the invention, further typical examples thereof are amino acids (e.g. glycine, alanine, arginine, serine, threonine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene, lutein) or derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, boldin, boldo extract, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of gum benzoin, rutic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, superoxide dismutase, zinc and derivatives thereof (e.g. $ZnO$, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention.

The further UV light protection factors or antioxidants can be added in amounts of from 0.01 to 25% by weight, preferably 0.03 to 10% by weight and in particular 0.1 to 5% by weight, based on the total amount in the preparations.

The extracts from the leaves of the plant *Argania spinosa* are effective, for the purposes of the invention, as antiinflammatory care agent which can heal inflammation of the skin or which can prevent inflammation. The inflammations here can have a very wide variety of causes. In particular, it is possible to treat inflammations which are induced by UV radiation, skin contaminations or bacterially or hormonally caused changes in the skin, e.g. acne.

The extracts from the leaves of the plant *Argania spinosa* are effective, for the purposes of the invention, as antimicrobial agents, in particular against every type of bacterially caused skin change.

This type of skin change includes infection by bacteria of a very wide variety of types and genera, such as, for example, staphylococci, streptococci, streptomycetes and/or propione bacteria.

The extracts from the leaves of the plant *Argania spinosa* are effective, for the purposes of the invention, against skin aging, in particular against every type of wrinkling and line formation. Another name for this type of care agent is also antiaging agent. The uses include a slowing of the aging processes of the skin. The aging phenomena can have a very wide variety of causes. In particular, these aging phenomena can be caused on the basis of apoptosis, damage to the skin induced by UV radiation or by the destruction of proteins endogenous to the skin, such as, for example, collagen or elastane.

The extracts according to the invention from extracts from the leaves of the plant *Argania spinosa* act as protease-inhibiting agent, in particular as MMP- and/or collagenase- and/or elastase-inhibiting agent and preferably as plasmin inhibitors. MMP is understood as meaning matrix metalloproteases. Matrix metalloproteases include, inter alia, collagenase, but also a certain type of elastase. The activity of the enzymes is dependent on metal ions, often $Zn^{2+}$ ions. The elastase which occurs predominantly belongs to the group of serine proteases. Their catalytic reaction is based on another mechanism. These proteases (collagenase and the various elastases) catalyze the fragmentation and destruction of the dermal macromolecules, such as proteoglycan, collagen and elastin, and thereby lead to aging of the skin and to the effects of natural skin aging following UV radiation.

In the case of inflammatory processes in the skin, the macrophages and polymorphonuclear neutrophilic granulocytes release proteases, such as, for example, the serine protease elastase or matrix metalloproteases (MMP) such as collagenase and another elastin-degrading elastase which is a type of MMP. In addition, in older people or following UV radiation interstitial collagenases, also referred to as MMP-1, are released by the dermal fibroblasts.

Human tissue contains inhibitors of these matrix metalloproteases, whose formation and concentration decreases with age. Their name is abbreviated to TIMP (tissue inhibitor of metalloprotease). The extracts according to the invention are able to stimulate the formation of these naturally occurring inhibitors.

As well as the already mentioned effects of the extracts from the leaves of the plant *Argania spinosa*, positive effects were found in the influencing of melanogenesis. Melanogenesis refers to the natural synthesis of melanin in the cells, specifically the melanocytes. This natural pigmenting can be influenced by intervening in the reaction chain of the oxidation of tyrosine via L-DOPA to give melanin. Skin-lightening effects are achieved by inhibiting melanogenesis, whereas stimulation of melanogenesis may lead to increased pigmentation. The aqueous/alcoholic extracts from the leaves of the plant *Argania spinosa*, in particular aqueous/ethanolic extracts, exhibit stimulation of melanogenesis. These effects permit the use as pigmenting agent or as self-tanning agent.

As well as the various extracts from the leaves of the plant *Argania spinosa*, the preparations can comprise further self-tanning agents or tyrosinase inhibitors. A suitable self-tanning agent is dihydroxyacetone. Suitable tyrosinase inhibitors, which prevent the formation of melanin and are used in depigmentation agents, are, for example, arbutin, ferulic acid, kojic acid, cumaric acid and ascorbic acid (vitamin C).

The use of the extracts according to the invention as protective and restorative care agents is in principle possible for all preparations which are used for prevention against damage or in the case of damage to the skin and/or the hair and thus in skincare and haircare. Another use in this field is the application in cases of sensitive skin damaged by allergy or other causes. The damage to the skin can have a very wide variety of causes.

The preparations according to the invention can be used for the preparation of cosmetic and/or dermopharmaceutical preparations, such as, for example, hair shampoos, hair lotions, foam baths, shower baths, creams, gels, lotions, alcoholic and aqueous/alcoholic solutions, emulsions, wax/fat compositions, stick preparations, powders or ointments. Furthermore, the preparations for oral application according to the invention can also be incorporated into tablets, dragees, capsules, juices, solutions and granules. These preparations can also comprise, as further auxiliaries and additives, mild surfactants, oily bodies, emulsifiers, pearlescent waxes, bodying agents, thickeners, superfatting agents, stabilizers, polymers, silicone compounds, fats, waxes, lecithins, phospholipids, biogenic active ingredients, deodorants, antiperspirants, antidandruff agents, film formers, swelling agents, insect repellents, hydrotropes, solubilizers, preservatives, perfume oils, dyes and the like.

Surfactants

Surface-active substances which may be present are anionic, nonionic, cationic and/or amphoteric or amphoteric surfactants, the content of which in the compositions is usually about 1 to 70% by weight, preferably 5 to 50% by weight and in particular 10 to 30% by weight. Typical examples of anionic surfactants are soaps, alkylbenzenesulfonates, alkanesulfonates, olefin sulfonates, alkyl ether sulfonates, glycerol ether sulfonates, α-methyl ester sulfonates, sulfo fatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulfates, protein fatty acid condensates (in particular wheat-based vegetable products) and alkyl (ether) phosphates. If the anionic surfactants contain polyglycol ether chains, these may have a conventional homolog distribution, but preferably have a narrowed homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucoronic acid derivatives, fatty acid N-alkylglucamides, protein hydrolysates (in particular wheat-based vegetable products), polyol fatty acid esters, sugar esters, sorbitan esters, polysorbates and amine oxides. If the nonionic surfactants contain polyglycol ether chains, these may have a conventional homolog distribution, but preferably have a narrowed homolog distribution. Typical examples of cationic surfactants are quaternary ammonium compounds, such as, for example, dimethyldistearylammonium chloride, and ester quats, in particular quaternized fatty acid trialkanolamine ester salts. Typical examples of amphoteric or zwitterionic surfactants are alkylbetaines, alkylamidobetaines, aminopropionates, aminoglycinates, imidazoliniumbetaines and sulfobetaines. Said surfactants are exclusively known compounds. With regard to structure and preparation of these substances, reference may be made to relevant review works, for example, J. Falbe (ed.), "Surfactants in Consumer Products", Springer Verlag, Berlin, 1987, pp. 54–124 or J. Falbe (ed.), "Katalysatoren, Tenside und Mineralöladditive", Thieme Verlag, Stuttgart, 1978, pp. 123–217. Typical examples of particularly suitable mild, i.e. particularly skin-compatible surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefinsulfonates, ether carboxylic acids, alkyl oligoglucosides, fatty acid glucamides, alkylamidobetaines, amphoacetals and/or protein fatty acid condensates, the latter preferably based on wheat proteins.

Oily Bodies

Suitable oily bodies are, for example, Guerbet alcohols based on fatty alcohols having 6 to 18, preferably 8 to 10, carbon atoms, esters of linear $C_6$–$C_{22}$-fatty acids with linear or branched $C_6$–$C_{22}$-fatty alcohols or esters of branched $C_6$–$C_{13}$-carboxylic acids with linear or branched $C_6$–$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$–$C_{22}$-fatty acids with branched alcohols, in particular 2-ethylhexanol, esters of $C_{18}$–$C_{38}$-alkylhydroxycarboxylic acids with linear or branched $C_6$–$C_{22}$-fatty alcohols (cf. DE 19756377 A1), in particular dioctyl malates, esters of linear and/or branched fatty acids with polyhydric alcohols (such as, for example, propylene glycol, dimerdiol or trimertriol) and/or Guerbet alcohols, triglycerides based on $C_6$–$C_{10}$-fatty acids, liquid mono-/di-/triglyceride mixtures based on $C_6$–$C_{18}$-fatty acids, esters of $C_6$–$C_{22}$-fatty alcohols and/or Guerbet alcohols with aromatic carboxylic acids, in particular benzoic acid, esters of $C_2$–$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$–$C_{22}$-fatty alcohol carbonates, such as, for example, dicaprylyl carbonates (Cetiol® CC), Guerbet carbonates based on fatty alcohols having 6 to 18, preferably 8 to 10, carbon atoms, esters of benzoic acid with linear and/or branched $C_6$–$C_{22}$-alcohols (e.g. Finsolv® TN), linear or branched, symmetrical or unsymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicon methicone types, inter alia) and/or aliphatic or naphthenic hydrocarbons, such as, for example, such as squalane, squalene or dialkylcyclohexanes.

Emulsifiers

Suitable emulsifiers are, for example, nonionogenic surfactants from at least one of the following groups:

addition products of from 2 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group, and onto alkylamines having 8 to 22 carbon atoms in the alkyl radical;

alkyl and/or alkenyl oligoglycosides having 8 to 22 carbon atoms in the alk(en)yl radical and the ethoxylated analogs thereof;

addition products of from 1 to 15 mol of ethylene oxide onto castor oil and/or hydrogenated castor oil;

addition products of from 15 to 60 mol of ethylene oxide onto castor oil and/or hydrogenated castor oil;

partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mol of ethylene oxide;

partial esters of polyglycerol (average degree of self-condensation 2 to 8), polyethylene glycol (molecular weight 400 to 5 000), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mol of ethylene oxide;

mixed esters of pentaerythritol, fatty acids, citric acid and fatty alcohol as in German Patent 1165574 and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof;

wool wax alcohols;

polysiloxane-polyalkyl-polyether copolymers and corresponding derivatives;

block copolymers, e.g. polyethylene glycol-30 dipolyhydroxystearates;

polymer emulsifiers, e.g. Pemulen grades (TR-1, TR-2) from Goodrich;

polyalkylene glycols, and glycerol carbonate.

The addition products of ethylene oxide and/or of propylene oxide onto fatty alcohols, fatty acids, alkylphenols or onto castor oil are known, commercially available products. These are homolog mixtures whose average degree of alkoxylation corresponds to the ratio of the amounts of ethylene oxide and/or propylene oxide and substrate with which the addition reaction is carried out. $C_{12/18}$-fatty acid mono- and diesters of addition products of ethylene oxide onto glycerol are known from German Patent 2024051 as refatting agents for cosmetic preparations.

Alkyl and/or alkenyl oligoglycosides, their preparation and their use are known from the prior art. They are prepared, in particular, by reacting glucose or oligosaccharides with primary alcohols having 8 to 18 carbon atoms. With regard to the glycoside radical, both monoglycosides, in which a cyclic sugar radical is glycosidically bonded to the fatty alcohol, and also oligomeric glycosides having a degree of oligomerization of up to, preferably, about 8, are suitable. The degree of oligomerization here is a statistical average value which is based on a homolog distribution customary for such technical-grade products.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid moglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride, and the technical-grade mixtures thereof which may also comprise small amounts of triglyceride as a minor product of the preparation process. Likewise suitable are addition products of 1 to 30 mol, preferably 5 to 10 mol, of ethylene oxide onto said partial glycerides.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Likewise suitable are addition products of 1 to 30 mol, preferably 5 to 10 mol, of ethylene oxide onto said sorbitan esters.

Typical examples of suitable polyglycerol esters are polyglyceryl-2 dipolyhydroxystearate (Dehymuls® PGPH), polyglycerol-3 diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (Polyglycerol Caprate T2010/90), polyglyceryl-3 cetyl ether (Chimexane® NL), polyglyceryl-3 distearate (Cremophor® GS 32) and polyglyceryl polyricinoleate (Admul® WOL 1403), polyglyceryl dimerate isostearate, and mixtures thereof. Examples of further suitable polyol esters are the mono-, di- and triesters, optionally reacted with 1 to 30 mol of ethylene oxide, of trimethylolpropane or pentaerythritol with lauric acid, coconut fatty acid, tallow fatty acid, palmitic acid, stearic acid, oleic acid, behenic acid and the like.

Furthermore, zwitterionic surfactants can be used as emulsifiers. The term "zwitterionic surfactants" refers to those surface-active compounds which carry at least one quaternary ammonium group and at least one carboxylate and one sulfonate group in the molecule. Particularly suitable zwitterionic surfactants are the betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethyl-carboxymethyl glycinate. Particular preference is given to the fatty acid amide derivative known under the CTFA name Cocamidopropyl Betaine. Likewise suitable emulsifiers are ampholytic surfactants. The term "ampholytic surfactants" means those surface-active compounds which, apart from a $C_{8/18}$-alkyl or -acyl group in the molecule, contain at least one free amino group and at least one —COOH or —$SO_3H$ group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkyl aminopropionate, cocoacylaminoethyl aminopropionate and $C_{12/18}$-acylsarcosine. Finally, cationic surfactants are also suitable emulsifiers, those of the ester quat type, preferably methylquaternized difatty acid triethanolamine ester salts, being particularly preferred.

Fats and Waxes

Typical examples of fats are glycerides, i.e. solid or liquid vegetable or animal products which consist essentially of mixed glycerol esters of higher fatty acids, suitable waxes are inter alia natural waxes, such as, for example, candelilla wax, carnauba wax, japan wax, esparto grass wax, cork wax, guaruma wax, rice germ oil wax, sugarcane wax, ouricury wax, montan wax, beeswax, shellac wax, spermaceti, lanolin (wool wax), uropygial grease, ceresin, ozokerite (earth wax), petrolatum, paraffin waxes, microcrystalline waxes; chemically modified waxes (hard waxes), such as, for example, montan ester waxes, sasol waxes, hydrogenated jojoba waxes, and synthetic waxes, such as, for example, polyalkylene waxes and polyethylene glycol waxes. In addition to the fats, suitable additives are also fat-like substances, such as lecithins and phospholipids. The term lecithins is understood by the person skilled in the art as meaning those glycerophospholipids which form from fatty acids, glycerol, phosphoric acid and choline by esterification. Lecithins are thus frequently also known as phosphatidylcholines (PC). Examples of natural lecithins which may be mentioned are the cephalins, which are also referred to as phosphatidic acids and represent derivatives of 1,2-diacyl-sn-glycerol-3-phosphoric acids. By contrast, phospholipids are usually understood as meaning mono- and, preferably, diesters of phosphoric acid with glycerol (glycerophosphates), which are generally considered to be fats. In addition, sphingosines and sphingolipids are also suitable.

Pearlescent Waxes

Examples of suitable pearlescent waxes are: alkylene glycol esters, specifically ethylene glycol distearate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates, which have a total of at least 24 carbon atoms, specifically laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Bodying Agents and Thickeners

Suitable bodying agents are primarily fatty alcohols or hydroxy fatty alcohols having 12 to 22, and preferably 16 to 18, carbon atoms, and also partial glycerides, fatty acids or hydroxy fatty acids. Preference is given to a combination of these substances with alkyl oligoglucosides and/or fatty acid N-methylglucamides of identical chain length and/or polyglycerol poly-12-hydroxystearates. Suitable thickeners are, for example, Aerosil grades (hydrophilic silicas), polysaccharides, in particular xanthan gum, guar gum, agar agar, alginates and Tyloses, carboxymethylcellulose and hydroxyethylcellulose, and also relatively high molecular weight polyethylene glycol mono- and diesters of fatty acids, polyacrylates (e.g. Carbopols® and Pemulen grades from Goodrich; Synthalens® from Sigma; Keltrol grades from Kelco; Sepigel grades from Seppic; Salcare grades from Allied Colloids), polyacrylamides, polymers, polyvinyl alcohol and polyvinylpyrrolidone, surfactants, such as, for example, ethoxylated fatty acid glycerides, esters of fatty acids with polyols such as, for example, pentaerythritol or trimethylolpropane, fatty alcohol ethoxylates having a narrowed homolog distribution or alkyl oligoglucosides, and electrolytes such as sodium chloride and ammonium chloride.

Superfatting Agents

Superfatting agents which can be used are substances such as, for example, lanolin and lecithin, and polyethoxylated or acylated lanolin and lecithin derivatives, polyol fatty acid esters, monoglycerides and fatty acid alkanolamides, the latter also serving as foam stabilizers.

Stabilizers

Stabilizers which can be used are metal salts of fatty acids, such as, for example, magnesium, aluminum and/or zinc stearate or ricinoleate.

Polymers

Suitable cationic polymers are, for example, cationic cellulose derivatives, such as, for example, a quaternized hydroxyethylcellulose obtainable under the name Polymer JR 400® from Amerchol, cationic starch, copolymers of diallylammonium salts and acrylamides, quaternized vinylpyrrolidone-vinylimidazole polymers, such as, for example, Luviquat® (BASF), condensation products of polyglycols and amines, quaternized collagen polypeptides, such as, for example, lauryldimonium hydroxypropyl hydrolyzed collagen (Lamequat® L/Grünau), quaternized wheat polypeptides, polyethyleneimine, cationic silicone polymers, such as, for example, amodimethicones, copolymers of adipic acid and dimethylaminohydroxypropyldiethylenetriamine (Cartaretins®/Sandoz), copolymers of acrylic acid with dimethyldiallylammonium chloride (Merquat® 550/Chemviron), polyaminopolyamides, as described, for example, in FR 2252840 A, and crosslinked water-soluble polymers thereof, cationic chitin derivatives, such as, for example, quaternized chitosan, optionally in micro-crystalline dispersion, condensation products from dihaloalkyls, such as, for example, dibromobutane with bisdialkylamines, such as, for example, bis-dimethylamino-1,3-propane, cationic guar gum, such as, for example, Jaguar® CBS, Jaguar® C-17, Jaguar® C-16 from Celanese, quaternized ammonium salt polymers, such as, for example, Mirapol® A-15, Mirapol® AD-1, Mirapol® AZ-1 from Miranol.

Suitable anionic, zwitterionic, amphoteric and nonionic polymers are, for example, vinyl acetate-crotonic acid copolymers, vinylpyrrolidone-vinyl acrylate copolymers, vinyl acetate-butyl maleate-isobornyl acrylate copolymers, methyl vinyl ether-maleic anhydride copolymers and esters thereof, uncrosslinked polyacrylic acids and polyacrylic acids crosslinked with polyols, acrylamidopropyltrimethylammonium chloride-acrylate copolymers, octylacrylamide-methyl methacrylate-tert-butylaminoethyl methacrylate-2-hydroxypropyl methacrylate copolymers, polyvinylpyrrolidone, vinylpyrrolidone-vinyl acetate copolymers, vinylpyrrolidone-dimethylaminoethyl methacrylate-vinylcaprolactam terpolymers, and optionally derivatized cellulose ethers and silicones. Further suitable polymers and thickeners are listed in Cosm. Toil. 108, 95 (1993).

Silicone Compounds

Suitable silicone compounds are, for example, dimethylpolysiloxanes, methylphenylpolysiloxanes, cyclic silicones, and amino-, fatty-acid-, alcohol-, polyether-, epoxy-, fluorine-, glycoside- and/or alkyl-modified silicone compounds, which can either be liquid or in resin form at room temperature. Also suitable are simethicones, which are mixtures of dimethicones having an average chain length of from 200 to 300 dimethylsiloxane units and hydrogenated silicates. A detailed review of suitable volatile silicones can additionally be found in Todd et al., Cosm. Toil. 91, 27 (1976).

Biogenic Active Ingredients

Within the scope of the invention, biogenic active ingredients are additionally understood as meaning those which do not arise from the plant *Argania spinosa*, such as, for example, tocopherol acetate, tocopherol palmitate, ascorbic acid, (deoxy)ribonucleic acid and fragmentation products thereof, retinol, bisabolol, allantoin, phytantriol, panthenol, AHA acids, amino acids, ceramides, pseudoceramides, essential oils, further plant extracts and additional vitamin complexes.

Deodorants and Antimicrobial Agents

Cosmetic deodorants counteract, mask or remove body odors. Body odors arise as a result of the effect of skin bacteria on apocrine perspiration, with the formation of degradation products which have an unpleasant odor. Accordingly, deodorants comprise active ingredients which act as antimicrobial agents, enzyme inhibitors, odor absorbers or odor masking agents. Suitable antimicrobial agents are, in principle, all substances effective against gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxydiphenyl ether (triclosan), 4-chloro-3,5-dimethylphenol, 2,2'-methylenebis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen® CAT). The substances inhibit enzyme activity, thereby reducing the formation of odor. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Suitable odor absorbers are substances which are able to absorb and largely retain odor-forming compounds. They lower the partial pressure of the individual components, thus also reducing their rate of diffusion. It is important that in this process perfumes must remain unimpaired. Odor absorbers are not effective against bacteria. They comprise, for example, as main constituent, a complex zinc salt of ricinoleic acid or specific, largely odor-neutral fragrances which are known to the person skilled in the art as "fixatives", such as, for example, extracts of labdanum or styrax or certain abietic acid derivatives. The odor masking agents are fragrances or perfume oils, which, in addition to their function as odor masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal raw materials, such as, for example, civet and castoreum. Typical synthetic fragrance compounds are products of the ester, ether, aldehyde, ketone, alcohol and hydrocarbon type. Fragrance compounds of the ester type are, for example, benzyl acetate, p-tertbutylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linalool, phenylethyl alcohol and terpineol, and the hydrocarbons include mainly the terpenes and balsams. Preference is, however, given to using mixtures of different fragrances which together produce a pleasing fragrance note. Ethereal oils of relatively low volatility, which are mostly used as aroma components, are also suitable as perfume oils, e.g. sage oil, camomile oil, oil of cloves, melissa oil, mint oil, cinnamon leaf oil, linden flower oil, juniper berry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Antiperspirants reduce the formation of perspiration by influencing the activity of the eccrine sweat glands, thus counteracting underarm wetness and body odor. Aqueous or anhydrous formulations of antiperspirants typically comprise the following ingredients:

astringent active ingredients,
oil components,
nonionic emulsifiers,
coemulsifiers,
bodying agents,
auxiliaries, such as, for example, thickeners or complexing agents, and/or
nonaqueous solvents, such as, for example, ethanol, propylene glycol and/or glycerol.

Suitable astringent antiperspirant active ingredients are primarily salts of aluminum, zirconium or of zinc. Such suitable antihydrotic active ingredients are, for example, aluminum chloride, aluminum chlorohydrate, aluminum dichlorohydrate, aluminum sesquichlorohydrate and complex compounds thereof, e.g. with 1,2-propylene glycol, aluminum hydroxyallantoinate, aluminum chloride tartrate, aluminum zirconium trichlorohydrate, aluminum zirconium tetrachlorohydrate, aluminum zirconium pentachlorohydrate and complex compounds thereof, e.g. with amino acids, such as glycine. In addition, customary oil-soluble and water-soluble auxiliaries may be present in antiperspirants in relatively small amounts. Such oil-soluble auxiliaries may, for example, be:

anti-inflammatory, skin-protective or perfumed ethereal oils,
synthetic skin-protective active ingredients and/or
oil-soluble perfume oils.

Customary water-soluble additives are, for example, preservatives, water-soluble fragrances, pH regulators, e.g. buffer mixtures, water-soluble thickeners, e.g. water-soluble natural or synthetic polymers, such as, for example, xanthan gum, hydroxyethylcellulose, polyvinylpyrrolidone or high molecular weight polyethylene oxides.

Film Formers

Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof, and similar compounds.

Antidandruff Active Ingredients

Suitable antidandruff active ingredients are piroctone olamine (1-hydroxy-4-methyl-6-(2,4,4-trimethylpentyl)-2-(1H)-pyridinone monoethanolamine salt), Baypival® (climbazole), Ketoconazole®, (4-acetyl-1-{-4-[2-(2,4-dichlorophenyl) r-2-(1H-imidazol-1-ylmethyl)-1,3-dioxylan-c-4-ylmethoxyphenyl}piperazine, ketoconazole, elubiol, selenium disulfide, colloidal sulfur, sulfur polyethylene glycol sorbitan monooleate, sulfur ricinol polyethoxylate, sulfur tar distillates, salicyclic acid (or in combination with hexachlorophene), undecylenic acid monoethanolamide sulfosuccinate Na salt, Lamepon® UD (protein undecylenic acid condensate), zinc pyrithione, aluminum pyrithione and magnesium pyrithione/dipyrithione magnesium sulfate.

Swelling Agents

The swelling agents for aqueous phases may be montmorillonites, clay mineral substances, Pemulen, and alkyl-modified Carbopol grades (Goodrich). Other suitable polymers and swelling agents are given in the review by R. Lochhead in Cosm. Toil. 108, 95 (1993).

Insect Repellents

Suitable insect repellents are N,N-diethyl-m-toluamide, 1,2-pentanediol or ethyl butylacetylaminopropionate.

Hydrotropes

To improve the flow behavior, hydrotropes, such as, for example, ethanol, isopropyl alcohol, or polyols, can also be used. Polyols which are suitable here preferably have 2 to 15 carbon atoms and at least two hydroxyl groups. The polyols can also contain further functional groups, in particular amino groups, or be modified with nitrogen. Typical examples are glycerol;
alkylene glycols, such as, for example, ethylene glycol, diethylene glycol, propylene glycol, butylene glycol, hexylene glycol, and polyethylene glycols with an average molecular weight of from 100 to 1 000 daltons;
technical-grade oligoglycerol mixtures with a degree of self-condensation of from 1.5 to 10, such as, for example, technical-grade diglycerol mixtures with a diglycerol content of from 40 to 50% by weight;
methylol compounds, such as, in particular, trimethylolethane, trimethylolpropane, trimethylolbutane, pentaerythritol and dipentaerythritol;
lower alkyl glucosides, in particular those with 1 to 8 carbon atoms in the alkyl radical, such as, for example, methyl and butyl glucoside;
sugar alcohols with 5 to 12 carbon atoms, such as, for example, sorbitol or mannitol,
sugars with 5 to 12 carbon atoms, such as, for example, glucose or sucrose;
amino sugars, such as, for example, glucamine;
dialcohol amines, such as diethanolamine or 2-amino-1, 3-propanediol.

Preservatives

Suitable preservatives are, for example, phenoxyethanol, formaldehyde solution, parabenes, pentanediol or sorbic acid, and the other classes of substance listed in Annex 6, Part A and B of the Cosmetics Directive.

Perfume Oils

Perfume oils which may be mentioned are mixtures of natural and synthetic fragrances. Natural fragrances are extracts from flowers (lily, lavender, rose, jasmine, neroli, ylang-ylang), stems and leaves (geranium, patchouli, petitgrain), fruits (aniseed, coriander, cumin, juniper), fruit peels (bergamot, lemon, orange), roots (mace, angelica, celery, cardamom, costus, iris, calmus), woods (pine wood, sandalwood, guaiac wood, cedarwood, rosewood), herbs and grasses (tarragon, lemon grass, sage, thyme), needles and branches (spruce, fir, pine, dwarf-pine), resins and balsams (galbanum, elemi, benzoin, myrrh, olibanum, opoponax). Also suitable are animal raw materials, such as, for example, civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bourgeonal, and the ketones include, for example, the ionones, $\alpha$-isomethylionone and methyl cedryl ketone, the alcohols include anethole, citronellol, eugenol, isoeugenol, geraniol, linalool, phenylethyl alcohol and terpineol, and the hydrocarbons include predominantly the terpenes and balsams. Preference is, however, given to using mixtures of different fragrances which together produce a pleasing fragrance note. Ethereal oils of relatively low volatility, which are mostly used as aroma components, are also suitable as perfume oils, e.g. sage oil, camomile oil, oil of cloves, melissa oil, mint oil, cinnamon leaf oil, linden blossom oil, juniper berry oil, vetiver oil, olibanum oil, galbanum oil, labolanum oil and lavandin oil. Preference is given to using bergamot oil, dihydromyrcenol, lilial, lyral, citronellol, phenylethyl alcohol, $\alpha$-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, $\beta$-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Dyes

Dyes which can be used are the substances which are approved and suitable for cosmetic purposes, as are summarized, for example, in the publication "Kosmetische Färbemittel" [Cosmetic Colorants] from the Farbstoffkommission der Deutschen Forschungsgemeinschaft [Dyes Commission of the German Research Council], Verlag Chemie, Weinheim, 1984, pp. 81–106. These dyes are normally used in concentrations of from 0.001 to 0.1% by weight, based on the total mixture.

EXAMPLES

1. Example

Extraction of the Plants with Distilled Water 0.3 kg of comminuted leaves of the plant *Argania spinosa* were transferred to a glass vessel, and 3 l of distilled water were poured onto them. The mixture was stirred for one hour at 80–90° C. The mixture was then left to cool to room temperature and centrifuged for 15 min at a speed of 5000 g. The supernatant colloidal liquid was separated off from the residue by filtration over deep-bed filters with an average porosity of 450 nm (from Seitz, Bordeaux, France) and then spray-dried. The yield of dry product calculated on the basis of the dry weight of the leaves used was 25.6% by weight.

2. Example

Extraction of the Plants with Aqueous Methanol

Example 1 was repeated, but the extraction was carried out with 1 l of 80% strength by weight aqueous methanol and 0.1 kg of comminuted leaves. The extraction was carried out with stirring for 1 h at boiling temperature under reflux and the extract was further processed as described. The filtration was carried out as described in example 1, but the residue was washed again with 100 ml of 80% strength by weight aqueous methanol. Then, firstly the alcohol was removed at 30° C. under reduced pressure and then the residue was spray-dried as described. The yield of dry product was 28.0% by weight, calculated on the basis of the dry weight of plants used.

3. Example

Extraction of the Plants with Aqueous Ethanol

Example 1 was repeated, but the extraction was carried out with 3 l of aqueous ethanol and 0.1 kg of leaves, where the volume ratio of ethanol to water was 6:4. The extraction was carried out with stirring for 1 h at boiling temperature under reflux and the extract was further processed as described. The filtration was carried out as described in example 1 and the residue was washed again with 0.30 l of ethanol. Then, firstly the alcohol was removed at 30° C. under reduced pressure and then the residue was spray-dried. The yield of dry product was 21.53% by weight, based on the dry weight of plants used.

4. Example

Antimicrobial Effectiveness

To determine the antimicrobial effectiveness, filter paper platelets 6 mm in size, which had been saturated with 20 µl of various test solutions (1% and 5%), were applied to the surface of an agar preparation freshly treated with *Staphylococcus aureus* (1.5 $10^6$ bacteria/ml). To prepare this agar preparation, an agar solution was suspended with 2–4 ml of inoculum, transferred to a Petri dish and dried at 37° C. for 20 min. The inoculum was obtained by anaerobic incubation of the *Staphylococcus aureus* bacteria for 18 hours. The effectiveness was analyzed by determining the average diameter of the areas within which no bacterial growth could be established.

The results are summarized in table 1:

TABLE 1

Effectiveness toward bacteria (data as diameter of inhibition zone in mm)

| Concentration [% by wt.] | Extract, example 1 | Extract, example 2 | Extract, example 3 |
| --- | --- | --- | --- |
| 1 | | | 7 |
| 5 | 14 | 12 | 7 |

The inhibition zones of 7 to 14 mm show a significant inhibition of the growth of *Staphylococcus aureus* bacteria in the vicinity of the filter platelets saturated with the extracts.

5. Example

Activity Toward Free Radicals

In a first test series, the suitability of the extracts against oxidative stress was analyzed. The extracts as in examples 1 to 3 were used, in each case in a concentration of 0.3% by weight. The first test substrate chosen was diphenylpicrylhydrazyl (DPPH), a purple-red colored stable radical which converts to its noncolored leuco derivative when brought into contact with free-radical scavengers. The color change can be monitored photometrically. The measurement results are summarized in table 2 ("DPPH test"), which gives the inhibition of DPPH in % absolute. In a further test, the hydroxylation of salicylic acid by hydroxyl radicals (from the reaction of hydrogen peroxide with iron(III) ions and EDTA) was investigated as reference system. This reaction too can be investigated photometrically since the hydroxylation product is reddish in color. The effect of the extracts on the formation of the hydroxysalicylic acid at an optical density of 490 nm was measured. The measurement results are likewise summarized in table 1, which again gives the inhibition in % absolute ("salicylic acid test"). In a third and final test, xanthine oxidase was chosen as the test system. Under oxidative stress, the enzyme brings about the conversion of purine bases, such as, for example, adenine or guanine into uronic acid, it being possible to detect and quantitatively determine the oxygen radicals which form as intermediates by reaction with luminol by means of luminescence. In the presence of substances with free-radical scavenging properties, the luminescence yield decreases. These results are also summarized in table 2; again, the inhibition is given in % absolute ("luminol test").

TABLE 2

Free-radical inhibition [% absolute]

| | DPHH test | Salicylic acid test | Luminol test |
| --- | --- | --- | --- |
| Extract as in example 1 | 83 | 62 | 100 |
| Extract as in example 2 | 100 | 65 | 100 |
| Extract as in example 3 | 88 | 57 | 100 |

The extracts of the leaves of *Argania spinosa* exhibited a high potential for scavenging free radicals and reactive oxygen and can, for this reason, be used in an excellent manner as antioxidants in cosmetic or dermo-pharmaceutical preparations.

6. Example

Cell-Protective Action Against UVA on Human Fibroblasts Cultivated In Vitro

Background: UVA rays penetrate into the dermis where they lead to oxidative stress, which is detected by lipoperoxidation of the cytoplasm membranes.

The lipoperoxides are degraded to malonaldialdehyde, which will crosslink many biological molecules such as proteins and nucleic bases (enzyme inhibition or mutagenesis).

Glutathione (GSH) is a peptide which is produced directly by the cells in order to counteract oxidative stress or harmful environmental influences, such as, for example, increased mercury or lead content. The content of GSH was determined in accordance with the Hissin method, described in Anal. Biochem., 74, 214–226, 1976.

Method: To carry out these tests, a defined culture medium (DMEM) with 10% fetal calf serum was inoculated with the fibroblasts, and the plant extract (in the defined medium with 2% serum) was added 72 hours after inoculation.

Following incubation for 48 hours at 37° C. and a $CO_2$ content of 5%, the culture medium was replaced by a sodium chloride solution, and the fibroblasts were irradiated with a UVA dose (20 J/cm$^2$; tubes: MAZDA FLUOR TFWN40).

When the irradiation was complete, the content of cell proteins and the proportion of GSH was determined, and the MDA level (malonaldialdehyde level) in the supernatant saline solution was determined quantitatively by reaction with thiobarbituric acid. The results are given as a percentage compared with the control without irradiation.

TABLE 3

Quantification of malonaldialdehyde, cell proteins and GSH in fibroblasts (results in % based on the control, average value from 2 experiments, each with three repetitions)

| Concentration (% by wt.) | MDA level | Content of cell proteins | Proportion of GSH |
| --- | --- | --- | --- |
| Control without UVA | 0 | 105 | 100 |
| UVA (20 J/cm$^2$) | 100 | 100 | 49 |

| Concentration (% by wt.) | MDA level | Content of cell proteins | Proportion of GSH |
| --- | --- | --- | --- |
| UVA + extract as in example 1 0.003% | 79 | 102 | 45 |
| UVA + extract as in example 2 0.001% | 42 | 117 | 83 |
| UVA + extract as in example 3 0.003% | 34 | 117 | 94 |

The results from table 3 show that the extracts from the leaves of the plant *Argania spinosa* according to the invention significantly reduce the degree of MDA in human fibroblasts which is induced by UVA rays. Furthermore, there is high activity to keep the proportion of GSH in human fibroblasts relatively constant following irradiation with UVA radiation. These results show a high capacity of extracts from the leaves of *Argania spinosa* for reducing harmful effects of oxidative stress on the skin.

7. Example

Antiinflammatory Properties In Vitro—UVB Light Protection

Cell-Protective Action Against UVB on Human Keratinocytes Cultivated in vitro

Background: UVB rays (from 280 to 320 nm) trigger inflammation (erythema, edema) by activating an enzyme, namely phospholipase A2 or PLA2, which removes arachidonic acid from the phospholipids of the plasma membrane. Arachidonic acid is the precursor of prostaglandins, which cause inflammation and cell membrane damage; the prostaglandins E2 (=PGE2) are formed by cyclooxygenase.

Method: The effect of UVB radiation was investigated on keratinocytes in vitro by determining the release of the cytoplasm enzyme LDH (lactate dehydrogenase). This enzyme serves as a marker for cell damage.

To carry out the tests, a defined medium (DMEM), which comprises 10% fetal calf serum, was inoculated with the keratinocytes and the plant extract (diluted with saline solution) was added 72 hours after inoculation.

The keratinocytes were then irradiated with a UVB dose (50 mJ/cm$^2$—tubes: DUKE GL40E).

Following further incubation for 1 day at 37° C. and at 5% $CO_2$, the LDH and the PGE2 content in the supernatant was determined. The content of LDH (lactate dehydrogenase) was determined by means of an enzyme reaction (kit used to investigate the LDH content from Roche). The content of PGE2 was determined using an ELISA test (ELISA kit from Roche). Following trypsin treatment, the cells were centrifuged and counted.

TABLE 4

Cell-protective action of a leaf extract of Argania spinosa against UVE rays; results in % based on the control, average value from 2 experiments, each with two repetitions

| Extract as in example 1 | Content of released LDH (%) |
|---|---|
| Control without UV | Number of keratinocytes (%) |
| Control with UVB (30 mJ/cm$^2$) | 49 | 100 |
| UVB + extract 0.001% | 73 | 11 |

The results of these tests show that an extract from the plant *Argania spinosa* according to the invention reduces the effect of UVB radiation on the number of keratinocytes. There is a reduction in the content of released LDH in the cytoplasm. The extracts described accordingly have the ability to reduce damage to cell membranes caused by UVB radiation, and exhibit an inhibiting effect against inflammations which are induced by UVB radiation.

8. Example

Inhibition of the Elastase Activity

Serine proteases, such as, for example, elastase or collagenase, bring about the degradation of elastin, proteoglycans and collagen and thus cause a weakening of the connective tissue. In the following test, the inhibiting properties of the extracts toward a pancreas elastase were investigated in two systems, firstly in a chromogenic synthetic substrate A and secondly in a natural substrate B (elastin/Congo Red). The amount of extracts used was 0.3% by weight, and the incubation time was 30 min (20° C.). The inhibition was monitored photometrically at 410 and 520 nm, and the standard used was α1-antitrypsin (=0% inhibition). The results are summarized in table 5.

TABLE 5

Elastase inhibition [% absolute]

| | Substrate A | Substrate B |
|---|---|---|
| α1-Antitrypsin | IC50 = 0.01% | IC50 = 0.034% |
| Extract as in example 1 | 51% | 18% |
| Extract as in example 2 | 57% | 66% |
| Extract as in example 3 | 100% | 6% |

The biochemical test of collagenase inhibition was realized with a collagenase from Chlostridium histolyticum in a chromogenic synthetic substrate C: FALGPA (furylacryloyl-Leu-Gly-Pro-Ala), a specific substrate for collagenase, which is not hydrolyzed by the enzyme. This substrate was obtained from SIGMA.

The amount of extracts used was 0.3% by weight, and the incubation time was 30 min (20° C.). The inhibition was investigated by determining the optical density "OD" at 234 nm.

TABLE 6

Collagenase inhibition [% absolute]

| | Substrate C |
|---|---|
| Cystein | IC50 = 1.56% |
| Extract as in example 1 | 76% |
| Extract as in example 2 | 100% |

The biochemical test for the inhibition of plasmin, a special serine protease, was determined against the positive standard aprotinin. For an extract as in example 2, an EC50 value of 2 µg/ml was determined. Thus, a concentration as low as 2 µg/ml of said leaf extract from *Argania spinosa* is sufficient to achieve a 50% inhibition of enzyme activity.

The extracts from the leaves of *Argania spinosa* exhibit high activity in the inhibition of the proteases elastase and collagenase.

9. Inhibition of Human MMP-1 Synthesis

The ability of leaf extracts from *Argania spinosa* to reduce the toxic effect of UVA rays was investigated. This in vitro test investigates the ability to reduce the content of matrix metalloproteinases, such as, for example, MMP-1, which are released by human fibroblasts following UVA radiation. More MMP are released under the influence of UVA radiation. UVA rays were chosen as the model since they penetrate into the dermis, where they induce oxidative stress, which accelerates skin aging. Furthermore, it is already known that the release of matrix metalloproteinases increases during the normal aging process of the skin. Inhibition of the MMP would thus counteract the aging process of the skin.

The in vitro system used was a culture of dermal fibroblasts, and the parameter determined was the release of MMP-1 from these fibroblasts under the influence of UV radiation.

To carry out the experiment, a fibroblast culture was prepared in a defined culture medium (DMEM) with fetal calf serum and inoculated 2–3 days later with the test substances. Following incubation for 24 h at 37° C. and a $CO_2$ level of 5% by volume, the nutrient medium was replaced with an electrolyte solution and the fibroblasts were damaged using a defined amount of UVA radiation (20 $J/cm^2$). After the end of the irradiation, the fibroblast culture was incubated again for 2 days, and then, on a sample of the supernatant of the culture solution, the content of MMP-1 and TIMP-1 was determined. The abbreviation TIMP is understood as meaning a naturally occurring inhibitor of the metalloproteinase under the name "tissue inhibitor of matrix metalloproteinase".

The MMP and TIMP were determined using two different kits, which are commercially available under the name RPN2610 and RPN2611 from Amersham. The results are summarized in table 7. The data given is the amount of MMP-1 and TIMP-1 in ng/ml from a test series with triple determination.

TABLE 7

Determination of the amount of MMP-1 and TIMP-1 in ng/ml

|  |  | MMP-1 in ng/ml | | TIMP-1 in ng/ml | |
| --- | --- | --- | --- | --- | --- |
|  | Concentration | without UVA radiation | UVA 20 $J/cm^2$ | without UVA radiation | UVA 20 $J/cm^2$ |
| Control |  | 49 | 199 | 50 | 28 |
| Dexamethasone | 0.1 μM | 2 | 7 | 39 | 19 |
| Extract as in ex. 1 | 0.0006% | 31 | 121 | 54 | 25 |
| Extract as in ex. 2 | 0.003% | 27 | 88 | 47 | 19 |
| Extract as in ex. 3 | 0.006% | 16 | 72 | 40 | 14 |

The extracts show that leaf extracts from *Argania spinosa* significantly reduce the spontaneous release of MMP-1 by human fibroblasts. Furthermore, they show that the extracts according to the invention permanently reduce the release of MMP-1 in the event of UVA irradiation.

A reduction in the content of TIMP-1 can be found for the extracts according to the invention and also for dexamethasone which, however, can be attributed to the fact that the content of MMP-1 was already reduced by the effect of the extracts or by dexamethasone.

These extracts exhibit great abilities for reducing the natural effects of skin aging or skin aging as a result of UV radiation.

10. Example

Influence on Melanogenesis

Background: The skin-lightening activity was investigated using an inhibition test on tyrosinase and an inhibition test on melanin synthesis on B16 melanocytes. Tyrosinase is the key enzyme in the synthesis of melanin in the melanocytes of the human skin. This enzyme catalyzes the first two stages of the conversion of tyrosine into melanin, i.e. the oxidation of tyrosine to give L-DOPA (dihydroxyphenylalanine) and then into dopachrome.

Method: 1. Tyrosinase inhibition: L-DOPA was mixed with tyrosinase and the extract to be tested. The optical density of the dopachrome was analyzed at 475 nm. The kinetics were then investigated and the concentration for a 50% strength inhibition (EC50) was determined.

2. Inhibition of melanogenesis on B16 melanocytes: The B16 melanocytes are cultivated in a defined medium (DMEM with 10% fetal calf serum) and incubated for 3 days at 37° C. and 5% CO2. The growth medium was replaced by the defined medium without calf serum, which comprised a certain content of the extracts to be tested. After further incubation for 3 days, the proportion of intact cells was determined via the content of cell proteins in accordance with the Bradford method (Anal. Biochem. 72, 248–254, 1976), and the content of melanin formed was determined by analyzing the optical density at 475 nm in accordance with the method described by Ando et al. 17th IFSCC Congress—Yokohama, 2, 909–918, 1992.

The comparison substance was hydroquinone.

The results were determined as activity index in the ratio of proportion of proteins to content of melanin: the greater the index, the higher the inhibition activity and the lower the stimulation of melanogenesis.

TABLE 8

Influence on melanogenesis

|  |  | Melanin synthesis | |
| --- | --- | --- | --- |
|  | Tyrosinase in tubo | Concentration (% by wt.) | Index |
| Hydroquinone | EC50 = 0.025% | 0.0003 | 2.21 |
| Extract as in example 3 | EC50 = 0.077% | 0.01 | 0.4 |

The results show a stimulation of the melanin synthesis for extracts as in example 3. This gives rise to the use of the extract as pigmenting agent.

11. Effect on the Survival Activity of Human Fibroblasts

To assess the cell activity, there are fundamental markers, which include MTT, proteins and glutathione.

The survival was evaluated by means of the following contents:

rate of the metabolized MTT (Methyl Thiazolyl Tetrazolium); the mitochondrial activity is determined by means of the MTT test. MTT is reduced by an enzyme of the respiration chain, succinate dehydrogenase, into formazan (Denizot F, Lang R, Rapid calorimetric assay for cell growth and survival. J. Immunol. Methods, 89, 271–277, 1986).

of proteins; the protein concentration of the cells was determined in accordance with Bradford (Bradford M. M. A rapid and sensitive method for the quantitation of microgram quantities of protein utilizing the principle of protein-dye binding. Anal. Biochem. (1977) vol. 72, pp. 248–254)

of glutathione (GSH), a peptide produced directly by the cell, for combating oxidative stress or various contaminants, such as, for example, heavy metals. Its synthesis requires ATP as energy source. GSH was determined in accordance with Hissin (Hissin P. J., Hilf R. A fluorometric method for determination of oxidised and reduced Glutathione in tissues. Analytical Biochemistry (1977) vol. 74, pp. 214–226).

Glutathione (GSH) is a peptide which is produced by cells in order to protect the cell against oxidative stress or heavy metals, such as, for example, lead or mercury. The three amino acids which are involved in the reduced form of GSH are in turn joined to specific cytoplasmatic enzymes which require ATP.

The increase in the GSH level has a positive influence on the activity of the glutathione-S-transferase, which represents a decontaminating enzyme.

Method: Human fibroblasts were inoculated in a nutrient medium (DMEM=Dulbecco Minimum Essential Medium from Life Technologie Sarl) with 10% fetal calf serum (from Dutcher) and incubated for 24 hours at 37° C. in a 5% $CO_2$ atmosphere.

The medium was then replaced by a suboptimum medium (without SVF), which comprised various extracts in varying concentrations (0.01; 0.03 and 0.1% by weight) in accordance with the description of the invention.

The results are given relative to an extract-free formulation for protein, MTT and GSH in the ratio and expressed as a percentage relative to the untreated control agent given as average value +/−SEM (error type of the average).

TABLE 9

Cell survival test-results in % based on the control without extract (average value of 2 assays in triple determination)

| | Concentration in % by weight | MTT | Proteins | GSH/ proteins |
|---|---|---|---|---|
| Control | 0 | 100 | 100 | 100 |
| Extract as in example 3 | 0.0001 | 91 | 102 | 102 |
| | 0.0003 | 71 | 92 | 114 |
| | 0.001 | 56 | 77 | 128 |

The table gives in each case the mitochondrial activity via the MTT, protein contents and the GSH contents, which were measured after three days for various concentrations of extracts. An extract from the leaves of the plant *Argania spinosa* as in example 3 with a concentration of 0.01% by weight is able to increase the GSH content in human fibroblasts by 28%.

The results show that the extracts from leaves of *Argania spinosa* are able to improve the metabolism (synthesis of glutathione) through the human fibroblasts, which clearly gives rise to an energy-saving, stimulating and "antiaging" activity of these extracts.

12. Example

Formulations of Cosmetic Compositions Comprising Extracts from the Leaves of the Plant *Argania spinosa*

The extracts obtained as in example 1 to 3 were used in the following formulations K1 to K21 according to the invention, and also 1 to 40. The cosmetic compositions prepared in this way displayed, compared with the comparison formulations C1, C2 and C3, very good skincare properties with simultaneously good skin compatibility. Moreover, the compositions according to the invention are stable against oxidative decomposition.

All of the substances with a registered trade name used and listed in tables 10–13 are trademarks and products of the COGNIS group.

TABLE 10

Soft cream formulations K1 to K7
(All data in % by weight based on the cosmetic composition)

| INCI name | K1 | K2 | K3 | K4 | K5 | K6 | K7 | C1 |
|---|---|---|---|---|---|---|---|---|
| Glyceryl Stearate (and) Ceteareth-12/20 (and) Cetearyl Alcohol (and) cetyl Palmitate | 8.0 | 8.0 | 8.0 | 8.0 | 8.0 | 8.0 | 8.0 | 8.0 |
| Cetearyl Alcohol | 2.0 | 2.0 | 2.0 | 2.0 | 2.0 | 2.0 | 2.0 | 2.0 |
| Dicaprylyl Ether | 2.0 | 2.0 | 2.0 | 2.0 | 2.0 | 2.0 | 2.0 | 2.0 |
| Cocoglycerides | 3.0 | 3.0 | 3.0 | 3.0 | 3.0 | 3.0 | 3.0 | 3.0 |
| Cetearyl Isononanoate | 3.0 | 3.0 | 3.0 | 3.0 | 3.0 | 3.0 | 3.0 | 3.0 |
| Glycerol (86% strength by wt.) | 3.0 | 3.0 | 3.0 | 3.0 | 3.0 | 3.0 | 3.0 | 3.0 |
| Extract as in example 1 | 0.5 | 0.5 | 0.5 | 0.5 | 0.5 | 0.5 | 0.5 | — |
| Tocopherol | | 0.5 | | | | | | |
| Allantoin | | | 0.2 | | | | | |
| Bisabolol | | | | 0.5 | | | | |
| Chitosan (Hydagen CMF) | | | | | 10.0 | | | |
| Deoxyribonucleic acid[1] | | | | | | 0.5 | | |
| Panthenol | | | | | | | 0.5 | |
| Water | Ad 100 | | | | | | | |

TABLE 11

Night cream formulations K8 to K14
(All data in % by weight based on the cosmetic composition)

| INCI name | K8 | K9 | K10 | K11 | K12 | K13 | K14 | C2 |
|---|---|---|---|---|---|---|---|---|
| Polyglyceryl-2 Dipolyhydroxystearate | 4.0 | 4.0 | 4.0 | 4.0 | 4.0 | 4.0 | 4.0 | 5.0 |
| Polyglyceryl-3 Diisostearate | 2.0 | 2.0 | 2.0 | 2.0 | 2.0 | 2.0 | 2.0 | 2.0 |
| Cera Alba | 2.0 | 2.0 | 2.0 | 2.0 | 2.0 | 2.0 | 2.0 | 2.0 |
| Zinc Stearate | 2.0 | 2.0 | 2.0 | 2.0 | 2.0 | 2.0 | 2.0 | 2.0 |
| Cocoglycerides | 3.0 | 3.0 | 3.0 | 3.0 | 3.0 | 3.0 | 3.0 | 3.0 |
| Cetearyl Isononanoate | 8.0 | 8.0 | 8.0 | 8.0 | 8.0 | 8.0 | 8.0 | 8.0 |
| Dicaprylyl Ether | 5.0 | 5.0 | 5.0 | 5.0 | 5.0 | 5.0 | 5.0 | 5.0 |
| Magnesium Sulfate | 1.0 | 1.0 | 1.0 | 1.0 | 1.0 | 1.0 | 1.0 | 1.0 |
| Glycerol (86% strength by wt.) | 5.0 | 5.0 | 5.0 | 5.0 | 5.0 | 5.0 | 5.0 | 5.0 |
| Extract as in example 1 | 0.5 | 0.5 | 0.5 | 0.5 | 0.5 | 0.5 | 0.5 | — |
| Tocopherol | | 0.5 | | | | | | |
| Allantoin | | | 0.2 | | | | | |
| Bisabolol | | | | 0.5 | | | | |
| Chitosan (Hydagen CMF) | | | | | 10.0 | | | |
| Deoxyribonucleic acid[1] | | | | | | 0.5 | | |
| Panthenol | | | | | | | 0.5 | |
| Water | Ad 100 | | | | | | | |

TABLE 12

W/O body lotion formulations K15 to K21
(All data in % by weight based on the cosmetic composition)

| INCI name | K15 | K16 | K17 | K18 | K19 | K20 | K21 | C3 |
|---|---|---|---|---|---|---|---|---|
| PEG-7 Hydrogenated Castor Oil | | | 7.0 | 7.0 | 7.0 | 7.0 | 7.0 | 7.0 |
| Decyl Oleate | 7.0 | 7.0 | 7.0 | 7.0 | 7.0 | 7.0 | 7.0 | 7.0 |
| Cetearyl Isononanoate | 7.0 | 7.0 | 7.0 | 7.0 | 7.0 | 7.0 | 7.0 | 7.0 |
| Glycerol (86% strength by wt.) | 5.0 | 5.0 | 5.0 | 5.0 | 5.0 | 5.0 | 5.0 | 5.0 |
| $MgSO_4 \cdot 7H_2O$ | 1.0 | 1.0 | 1.0 | 1.0 | 1.0 | 1.0 | 1.0 | 1.0 |
| Extract as in example 1 | 1.5 | 1.5 | 1.5 | 1.5 | 1.5 | 1.5 | 1.5 | — |
| Tocopherol | | 0.5 | | | | | | |
| Allantoin | | | 0.2 | | | | | |
| Bisabolol | | | | 0.5 | | | | |
| Chitosan (Hydagen CMF) | | | | | 10.0 | | | |
| Deoxyribonucleic acid[1] | | | | | | 0.5 | | |
| Panthenol | | | | | | | 0.5 | |
| Water | Ad 100 | | | | | | | |

[1] Deoxyribonucleic acid: molecular weight about 70 000, purity (determined by spectrophotometric measurement of the absorption at 260 nm and 280 nm): at least 1.7.

TABLE 13

Formulations
(All data in % by weight based on the cosmetic composition, water, preservatives make up to 100% by weight)

| Composition (INCI) | 1 | 2 | 3 | 4 | 5 | 6 | 7 | 8 | 9 | 10 |
|---|---|---|---|---|---|---|---|---|---|---|
| Texapon ® NBO Sodium Laureth Sulfate | — | — | — | — | — | — | 38.0 | 38.0 | 25.0 | — |
| Texapon ® SB 3 Disodium Laureth Sulfosuccinate | — | — | — | — | — | — | — | — | 10.0 | — |
| Plantacare ® 818 Coco Glucosides | — | — | — | — | — | — | 7.0 | 7.0 | 6.0 | — |
| Plantacare ® PS 10 Sodium Laureth Sulfate (and) Coco Glucosides | — | — | — | — | — | — | — | — | — | 16.0 |
| Dehyton ® PK 45 Cocamidopropyl Betaine | — | — | — | — | — | — | — | — | 10.0 | — |
| Dehyquart ® A Cetrimonium Chloride | 2.0 | 2.0 | 2.0 | 2.0 | 4.0 | 4.0 | — | — | — | — |
| Dehyquart L ® 80 Dicocoylmethylethoxymonium Methosulfate (and) Propylene Glycol | 1.2 | 1.2 | 1.2 | 1.2 | 0.6 | 0.6 | — | — | — | — |
| Eumulgin ® B2 Ceteareth-20 | 0.8 | 0.8 | — | 0.8 | — | 1.0 | — | — | — | — |
| Eumulgin ® VL 75 Lauryl Glucoside (and) Polyglyceryl-2 Polyhydroxystearate (and) Glycerol | — | — | 0.8 | — | 0.8 | — | — | — | — | — |
| Lanette ® O Cetearyl Alcohol | 2.5 | 2.5 | 2.5 | 2.5 | 3.0 | 2.5 | — | — | — | — |
| Cutina ® GMS Glyceryl Stearate | 0.5 | 0.5 | 0.5 | 0.5 | 0.5 | 1.0 | — | — | — | — |
| Cetiol ® HE PEG-7 Glyceryl Cocoate | 1.0 | — | — | — | — | — | — | — | 1.0 | — |
| Cetiol ® PGL Hexyldecanol (and) Hexyldecyl Laurate | — | 1.0 | — | — | 1.0 | — | — | — | — | — |
| Cetiol ® V Decyl Oleate | — | — | — | 1.0 | — | — | — | — | — | — |
| Eutanol ® G Octyldodecanol | — | — | 1.0 | — | 1.0 | — | — | — | — | — |

TABLE 13-continued

Formulations
(All data in % by weight based on the cosmetic composition, water, preservatives make up to 100% by weight)

| Composition | | | | | | | | | | |
|---|---|---|---|---|---|---|---|---|---|---|
| Nutrilan ® Keratin W Hydrolyzed Keratin | — | — | — | 2.0 | — | — | — | — | — | — |
| Lamesoft ® LMG Glyceryl Laurate (and) Potassium Cocoyl Hydrolyzed Collagen | — | — | — | — | — | — | 3.0 | 2.0 | 4.0 | — |
| Euperlan ® PK 3000 AM Glycol Distearate (and) Laureth-4 (and) Cocamidopropyl Betaine | — | — | — | — | — | — | 3.0 | 5.0 | 5.0 | |
| Generol ® 122 N Soy Sterol | — | — | — | — | 1.0 | 1.0 | — | — | — | — |
| Extract as in example 1–3 | 1.0 | 1.0 | 1.0 | 1.0 | 1.0 | 1.0 | 1.0 | 1.0 | 1.0 | 1.0 |
| Hydagen ® CMF Chitosan | 1.0 | 1.0 | 1.0 | 1.0 | 1.0 | 1.0 | 1.0 | 1.0 | 1.0 | 1.0 |
| Copherol ® 12250 Tocopherol Acetate | — | — | 0.1 | 0.1 | — | — | — | — | — | — |
| Arlypon ® F Laureth-2 | — | — | — | — | — | — | 3.0 | 3.0 | 1.0 | — |
| Sodium Chloride | — | — | — | — | — | — | — | 1.5 | — | 1.5 |

(1–4) hair rinse,
(5–6) hair treatment,
(7–8) shower preparation,
(9) shower gel,
(10) washing lotion Cosmetic preparations-continuation

| Composition (INCI) | 11 | 12 | 13 | 14 | 15 | 16 | 17 | 18 | 19 | 20 |
|---|---|---|---|---|---|---|---|---|---|---|
| Texapon ® NSO Sodium Laureth Sulfate | 20.0 | 20.0 | 12.4 | — | 25.0 | 11.0 | — | — | — | — |
| Texapon ® K 14 S Sodium Myreth Sulfate | — | — | — | — | — | — | — | — | 11.0 | 23.0 |
| Texapon ® SB 3 Disodium Laureth Sulfosuccinate | — | — | — | — | — | 7.0 | — | — | — | — |
| Plantacare ® 818 Coco Glucosides | 5.0 | 5.0 | 4.0 | — | — | — | — | — | 6.0 | 4.0 |
| Plantacare ® 2000 Decyl Glucoside | — | — | — | — | 5.0 | 4.0 | — | — | — | — |
| Plantacare ® PS 10 Sodium Laureth Sulfate (and) Coco Glucosides | — | — | — | 40.0 | — | — | 16.0 | 17.0 | — | — |
| Dehyton ® PK 45 Cocamidopropyl Betaine | 20.0 | 20.0 | — | — | 8.0 | — | — | — | — | 7.0 |
| Eumulgin ® B1 Ceteareth-12 | — | — | — | — | 1.0 | — | — | — | — | — |
| Eumulgin ® B2 Ceteareth-20 | — | — | — | 1.0 | — | — | — | — | — | — |
| Lameform ® TGI Polyglyceryl-3 Isostearate | — | — | — | 4.0 | — | — | — | — | — | — |
| Dehymuls ® PGPH Polyglyceryl-2 Dipolyhydroxystearate | — | — | 1.0 | — | — | — | — | — | — | — |
| Monomuls ® 90-L 12 Glyceryl Laurate | — | — | — | — | — | — | — | — | 1.0 | 1.0 |
| Cetiol ® HE PEG-7 Glyceryl Cocoate | — | 0.2 | — | — | — | — | — | — | — | — |
| Eutanol ® G Octyldodecanol | — | — | — | 0.3 | — | — | — | — | — | — |
| Nutrilan ® Keratin W Hydrolyzed Keratin | — | — | — | — | — | — | — | — | 2.0 | 2.0 |

TABLE 13-continued

Formulations
(All data in % by weight based on the cosmetic composition, water, preservatives make up to 100% by weight)

| | | | | | | | | | | |
|---|---|---|---|---|---|---|---|---|---|---|
| Nutrilan ® I Hydrolyzed Collagen | 1.0 | — | — | — | — | 2.0 | — | 2.0 | — | — |
| Lamesoft ® LMG Glyceryl Laurate (and) Potassium Cocoyl Hydrolyzed Collagen | — | — | — | — | — | — | — | — | 1.0 | — |
| Lamesoft ® 156 Hydrogenated Tallow Glyceride (and) Potassium Cocoyl Hydrolyzed Collagen | — | — | — | — | — | — | — | — | — | 5.0 |
| Gluadin ® WK Sodium Cocoyl Hydrolyzed Wheat Protein | 1.0 | 1.5 | 4.0 | 1.0 | 3.0 | 1.0 | 2.0 | 2.0 | 2.0 | — |
| Euperlan ® PK 3000 AM Glycol Distearate (and) Laureth-4 (and) Cocamidopropyl Betaine | 5.0 | 3.0 | 4.0 | — | — | — | — | 3.0 | 3.0 | — |
| Panthenol | — | — | 1.0 | — | — | — | — | — | — | — |
| Arlypon ® F Laureth-2 | 2.6 | 1.6 | — | 1.0 | 1.5 | — | — | — | — | — |
| Extract as in example 1–3 | 1.0 | 1.0 | 1.0 | 1.0 | 1.0 | 1.0 | 1.0 | 1.0 | 1.0 | 1.0 |
| Hydagen ® CMF Chitosan | 1.0 | 1.0 | 1.0 | 1.0 | 1.0 | 1.0 | 1.0 | 1.0 | 1.0 | 1.0 |
| Sodium Chloride | — | — | — | — | — | 1.6 | 2.0 | 2.2 | — | 3.0 |
| Glycerol (86% strength by weight) | — | 5.0 | — | — | — | — | — | 1.0 | 3.0 | — |

(11–14) two-in-one shower preparation,
(15–20) shampoo

Cosmetic preparations-continuation 2

| Composition (INCI) | 21 | 22 | 23 | 24 | 25 | 26 | 27 | 28 | 29 | 30 |
|---|---|---|---|---|---|---|---|---|---|---|
| Texapon ® NSO Sodium Laureth Sulfate | — | 30.0 | 30.0 | — | 25.0 | — | — | — | — | — |
| Plantacare ® 818 Coco Glucosides | — | 10.0 | — | — | 20.0 | — | — | — | — | — |
| Plantacare ® PS 10 Sodium Laureth Sulfate (and) Coco Glucosides | 22.0 | — | 5.0 | 22.0 | — | — | — | — | — | — |
| Dehyton ® PK 45 Cocamidopropyl Betaine | 15.0 | 10.0 | 15.0 | 15.0 | 20.0 | — | — | — | — | — |
| Emulgade ® SE Glyceryl Sterate (and) Ceteareth-12/20 (and) Cetearyl Alcohol (and) Cetyl Palmitate | — | — | — | — | — | 5.0 | 5.0 | 4.0 | — | — |
| Eumulgin ® B1 Ceteareth-12 | — | — | — | — | — | — | — | 1.0 | — | — |
| Lameform ® TGI Polyglyceryl-3 Isostearate | — | — | — | — | — | — | — | — | 4.0 | — |
| Dehymuls ® PGPH Polyglyceryl-2 Dipolyhydroxystearate | — | — | — | — | — | — | — | — | — | 4.0 |
| Monomuls ® 90-O 18 Glyceryl Oleate | — | — | — | — | — | — | — | — | 2.0 | — |
| Cetiol ® HE PEG-7 Glyceryl Cocoate | 2.0 | — | — | 2.0 | 5.0 | — | — | — | — | 2.0 |
| Cetiol ® OE Dicaprylyl Ether | — | — | — | — | — | — | — | — | 5.0 | 6.0 |

TABLE 13-continued

Formulations
(All data in % by weight based on the cosmetic composition, water, preservatives make up to 100% by weight)

| Composition | | | | | | | | | | |
|---|---|---|---|---|---|---|---|---|---|---|
| Cetiol ® PGL Hexyldecanol (and) Hexyldecyl Laurate | — | — | — | — | — | — | — | 3.0 | 10.0 | 9.0 |
| Cetiol ® SN Cetearyl Isononanoate | — | — | — | — | 3.0 | 3.0 | — | — | — | — |
| Cetiol ® V Decyl Oleate | — | — | — | — | 3.0 | 3.0 | — | — | — | — |
| Myritol ® 318 Coco Caprylate Caprate | — | — | — | — | — | — | — | 3.0 | 5.0 | 5.0 |
| Beeswax | — | — | — | — | — | — | — | — | 7.0 | 5.0 |
| Nutrilan ® Elastin E20 Hydrolyzed Elastin | — | — | — | — | — | 2.0 | — | — | — | — |
| Nutrilan ® I-50 Hydrolyzed Collagen | — | — | — | — | 2.0 | — | 2.0 | — | — | — |
| Gluadin ® AGP Hydrolyzed Wheat Gluten | 0.5 | 0.5 | 0.5 | — | — | — | — | 0.5 | — | — |
| Gluadin ® WK Sodium Cocoyl Hydrolyzed Wheat Protein | 2.0 | 2.0 | 2.0 | 2.0 | 5.0 | — | — | — | 0.5 | 0.5 |
| Euperlan ® PK 3000 AM Glycol Distearate (and) Laureth-4 (and) Cocamidopropyl Betaine | 5.0 | — | — | 5.0 | — | — | — | — | — | — |
| Arlypon ® F Laureth-2 | — | — | — | — | — | — | — | — | — | — |
| Extract as in example 1–3 | 1.0 | 1.0 | 1.0 | 1.0 | 1.0 | 1.0 | 1.0 | 1.0 | 1.0 | 1.0 |
| Hydagen ® CMF Chitosan | 1.0 | 1.0 | 1.0 | 1.0 | 1.0 | 1.0 | 1.0 | 1.0 | 1.0 | 1.0 |
| Magnesium Sulfate Heptahydrate | — | — | — | — | — | — | — | — | 1.0 | 1.0 |
| Glycerol (86% strength by weight) | — | — | — | — | — | 3.0 | 3.0 | 5.0 | 5.0 | 3.0 |

(21–25) foam bath,
(26) soft cream,
(27, 28) moisturizing emulsion,
(29, 30) night cream Cosmetic preparations - continuation 3

| Composition (INCI) | 31 | 32 | 33 | 34 | 35 | 36 | 37 | 38 | 39 | 40 |
|---|---|---|---|---|---|---|---|---|---|---|
| Dehymuls ® PGPH Polyglyceryl-2 Dipolyhydroxystearate | 4.0 | 3.0 | — | 5.0 | — | — | — | — | — | — |
| Lameform ® TGI Polyglyceryl-3 Diisostearate | 2.0 | 1.0 | — | — | — | — | — | — | — | — |
| Emulgade ® PL 68/50 Cetearyl Glucoside (and) Cetearyl Alcohol | — | — | — | — | 4.0 | — | — | — | 3.0 | — |
| Eumulgin ® B2 Ceteareth-20 | — | — | — | — | — | — | — | 2.0 | — | — |
| Tegocare ® PS Polyglyceryl-3 Methylglucose Distearate | — | — | 3.0 | — | — | 4.0 | — | — | — | — |
| Eumulgin VL 75 Polyglyceryl-2 Dipolyhydroxystearate (and) Lauryl Glucoside (and) Glycerol | — | — | — | — | — | 3.5 | — | — | 2.5 | — |
| Beeswax | 3.0 | 2.0 | 5.0 | 2.0 | — | — | — | — | — | — |
| Cutina ® GMS Glyceryl Stearate | — | — | — | — | — | 2.0 | 4.0 | — | — | 4.0 |

TABLE 13-continued

Formulations
(All data in % by weight based on the cosmetic composition, water, preservatives make up to 100% by weight)

| | | | | | | | | | | |
|---|---|---|---|---|---|---|---|---|---|---|
| Lanette ® O Cetearyl Alcohol | — | — | 2.0 | — | 2.0 | 4.0 | 2.0 | 4.0 | 4.0 | 1.0 |
| Antaron ® V 216 PVP/Hexadecene Copolymer | — | — | — | — | — | 3.0 | — | — | — | 2.0 |
| Myritol ® 818 Cocoglycerides | 5.0 | — | 10.0 | — | 8.0 | 6.0 | 6.0 | — | 5.0 | 5.0 |
| Finsolv ® TN C12/15 Alkyl Benzoate | — | 6.0 | — | 2.0 | — | — | 3.0 | — | — | 2.0 |
| Cetiol ® J 600 Oleyl Erucate | 7.0 | 4.0 | 3.0 | 5.0 | 4.0 | 3.0 | 3.0 | — | 5.0 | 4.0 |
| Cetiol ® OE Dicaprylyl Ether | 3.0 | — | 6.0 | 8.0 | 6.0 | 5.0 | 4.0 | 3.0 | 4.0 | 6.0 |
| Mineral Oil | — | 4.0 | — | 4.0 | — | 2.0 | — | 1.0 | — | — |
| Cetiol ® PGL Hexadecanol (and) Hexyldecyl Laurate | — | 7.0 | 3.0 | 7.0 | 4.0 | — | — | — | 1.0 | — |
| Panthenol/ Bisabolol | 1.2 | 1.2 | 1.2 | 1.2 | 1.2 | 1.2 | 1.2 | 1.2 | 1.2 | 1.2 |
| Extract as in example 1 to 3 | 1.0 | 1.0 | 1.0 | 1.0 | 1.0 | 1.0 | 1.0 | 1.0 | 1.0 | 1.0 |
| Hydagen ® CMF Chitosan | 1.0 | 1.0 | 1.0 | 1.0 | 1.0 | 1.0 | 1.0 | 1.0 | 1.0 | 1.0 |
| Copherol ® F 1300 Tocopherol/ Tocopheryl Acetate | 0.5 | 1.0 | 1.0 | 2.0 | 1.0 | 1.0 | 1.0 | 2.0 | 0.5 | 2.0 |
| Neo Heliopan ® Hydro Sodium Phenylbenzimidazole Sulfonate | 3.0 | — | — | 3.0 | — | — | 2.0 | — | 2.0 | — |
| Neo Heliopan ® 303 Octocrylene | — | 5.0 | — | — | — | 4.0 | 5.0 | — | — | 10.0 |
| Neo Heliopan ® BB Benzophenone-3 | 1.5 | — | — | 2.0 | 1.5 | — | — | — | 2.0 | — |
| Neo Heliopan ® E 1000 Isoamyl p-Methoxy-cinnamate | 5.0 | — | 4.0 | — | 2.0 | 2.0 | 4.0 | 10.0 | — | — |
| Neo Heliopan ® AV Octyl Methoxy cinnamate | 4.0 | — | 4.0 | 3.0 | 2.0 | 3.0 | 4.0 | — | 10.0 | 2.0 |
| Uvinul ® T 150 Octyl Triazone | 2.0 | 4.0 | 3.0 | 1.0 | 1.0 | 1.0 | 4.0 | 3.0 | 3.0 | 3.0 |
| Zinc Oxide | — | 6.0 | 6.0 | — | 4.0 | — | — | — | — | 5.0 |
| Titanium Dioxide | — | — | — | — | — | — | — | 5.0 | — | — |
| Glycerol (86% strength by weight) | 5.0 | 5.0 | 5.0 | 5.0 | 5.0 | 5.0 | 5.0 | 5.0 | 5.0 | 5.0 |

(31) W/O sunscreen cream,
(32–34) W/O sunscreen lotion,
(35, 38, 40) O/W sunscreen lotion,
(36, 37, 39) O/W sunscreen cream

The invention claimed is:

1. A method of enhancing the appearance of skin or hair of an individual comprising contacting the skin or the hair of the individual with a composition containing an extract of *Argania spinosa* leaves.

2. The method of claim 1 wherein the extract is present in the composition in an amount of from about 0.01 to 25% by weight, based on the dry weight of the composition.

3. The method of claim 1 wherein the extract is present in the composition in an amount of from about 0.03 to 5% by weight, based on the dry weight of the composition.

4. The method of claim 1 wherein the extract is present in the composition in an amount of from about 0.03 to 0.6% by weight, based on the dry weight of the composition.

* * * * *